United States Patent [19]

Soldati et al.

[11] 4,011,310
[45] Mar. 8, 1977

[54] DENTAL PROPHYLAXIS CONTAINING ALKYLAMINE FLUOROPHOSPHATES

[75] Inventors: Gianluigi Soldati, Mercerville; Ralph G. Eilberg, Cranbury; Helga Melger, Willingboro, all of N.J.; David A. Schlichting, Pound Ridge, N.Y.

[73] Assignee: Carter-Wallace, Inc., New York, N.Y.

[22] Filed: Oct. 20, 1975

[21] Appl. No.: 624,775

[52] U.S. Cl. .................. 424/52; 260/583 R; 260/583 P
[51] Int. Cl.$^2$ .......................... A61K 7/18
[58] Field of Search ............... 424/48–54; 260/583 R, 583 E, 583 G, 583 GG, 583 P, 584 R

[56] References Cited

UNITED STATES PATENTS 2,876,166  3/1959  Nebergall ..................... 424/52

OTHER PUBLICATIONS

Chem. Abstracts, vol. 76, 1972, paragraph 125934h, Mathey et al., "Direct Fluorination of Phosphoramides".

*Primary Examiner*—Lewis Gotts
*Assistant Examiner*—Cary Owens
*Attorney, Agent, or Firm*—Kevin B. Clarke

[57] ABSTRACT

Novel alkylamine fluorophosphates of the formula:

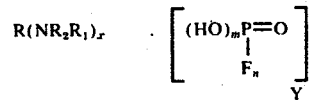

wherein R is a linear or branched alkyl group containing 1–20 carbon atoms; $R_1$ is lower alkyl or hydrogen, $R_2$ is alkyl or hydrogen; X is 1 or 2; Y is 1 when X=1; Y is 1 or 2 when X=2; $m$ and $n$ are positive whole integers whose sum is 3. When R, $R_1$ and $R_2$ are alkyl they can be substituted with an hydroxy group. The novel fluorophosphates have been found to be effective in reducing the acid solubility of tooth enamel.

16 Claims, No Drawings

DENTAL PROPHYLAXIS CONTAINING ALKYLAMINE FLUOROPHOSPHATES

The present invention relates to novel chemical compounds. More particularly, the invention relates to novel alkylamine mono- and difluorophosphates which have exhibited useful activity in the prevention of dental caries.

Much progress has been made during the past few years in the field of dental hygiene. However, the numerous and complex problems associated with the field create an ever increasing demand for new products designed to control or alleviate these problems.

Dental caries, i.e., tooth decay is a disease characterized by the dissolution of the mineral portion of the tooth apparently caused by acids produced by bacteria as an end product to their metabolism. If permitted to go unchecked, the disease ultimately attacks and penetrates the pulp chamber of the tooth resulting in pain and loss of viability of the tooth which may necessitate extraction or costly repair of the tooth.

Dental clinical investigators have long wrestled with such problems as alleviating and/or preventing dental caries. It is recognized that a clean tooth will not decay. However, it is also virtually impossible to keep the teeth continuously clean. Thus the initiation of carious lesions is usually accomplished in spite of the most vigorous cleansing regimen.

Several methods have been developed, with varying results, to reduce the incidence of tooth decay.

Antibiotics such as penicillin have been suggested for reducing dental caries and dentifrices containing penicillin have been tested and found to be effective. However, the antibiotics are not selective in the destruction of oral bacterial and destroy both the useful and harmful bacteria in the mouth indiscriminately resulting in a microbial imbalance in the mouth which can have serious consequences.

Further, it has been proposed to prevent dental caries by coating the tooth surfaces with a polymeric material. However, this proposal suffers from the following drawbacks; firstly, in order to obtain in a strong bond to the tooth surface, the teeth must first be etched with phosphoric acid; secondly, this treatment has been found to be effective only in young children who have yet to develop dental caries.

In addition, it has been found that the application of alkali metal or stannous fluorides to the teeth topically, in drinking water and in dentifrice preparations containing such fluoride compounds which release fluoride ions in water can be beneficial. While the fluoride compounds have been found to be effective, it has been found that the fluoride compounds tend to at least partially lose their effectiveness upon aging. This problem is of particular significance with respect to dental creams which contain water or other solvent material.

The use of fluoride ions for anticaries activity has been established for some time. In addition patents have been granted for the use of sodium fluoride (U.S. Pat. No. 2,876,166) and sodium monofluorophosphate (U.S. Pat. No. 3,227,618) in dentifrices to reduce the incidence of tooth decay.

In accordance with the present invention new compositions of matter showing use in the prevention of dental caries have been discovered. More specifically, the invention relates to alkylamine mono and difluorophosphates represented by the general formula:

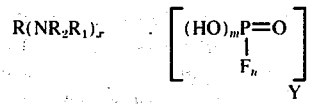

wherein R is a linear or branched alkyl group containing 1 to 20 carbon atoms, $R_1$ is lower alkyl containing 1–6 carbon atoms or hydrogen, $R_2$ is hydrogen or lower alkyl, $x$ is one or two, $m$ is two when $n =$ one, $m$ is one when $n$ is two; $y$ is 1 when $x$ is 1 and $y$ is 1 or 2 when $x$ is 2. When R, $R_1$ and $R_2$ represent an alkyl group they can be substituted with an hydroxy group.

In general, the compositions of the present invention may be prepared by combining aqueous or organic solutions of linear or branched alkylamines with aqueous or organic solutions of mono- or difluorophosphoric acids at temperatures of from about 5° to about 30° C. Typical of the primary secondary, and tertiary alkyl monoamines useful in preparing the compounds of the present invention are the methyl, dimethyl, ethyl, triethyl, propyl, isopropyl, butyl, dibutyl, isobutyl, t-butyl, pentyl, hexyl, heptyl, 2-aminoheptyl, octyl, decyl, dodecyl, octadecyl, and triethanolamines; useful diamines include but are not limited to the following:

1,3-diaminopropane; 1,4-diaminobutane; 1,5-diaminopentane; 1,7-diaminoheptane; 1,8-diaminooctane; 1,10-diaminodecane and 1,12-diaminododecane.

The alcohol solutions of acid and amine are the preferred form of reactants and the lower alcohols i.e., methanol, ethanol, propanol and isopropanol have been found to be particularly suitable.

The solutions are combined at a rate such that the temperature of the reactants and resulting reaction mixture is kept as nearly constant as is possible while the reaction is being carried out. The concentration of reactant in the solvent solution is not critical, however, it has been found that concentrations of one part reactant to ten parts solvent is suitable.

The following examples set out the best mode presently contemplated for preparing exemplary compounds of the present invention.

EXAMPLE I

To 50 g of laurylamine dissolved in 200 ml of isopropanol, there is added dropwise 29 g. of monofluorophosphoric acid in 100 ml isopropanol. The addition is carried out dropwise, under stirring, and at a temperature of 15° C. At the end of the addition the precipitate formed is dissolved by heating. On cooling, the solid material is collected by filtration, washed several times with isopropanol and dried over sulfuric acid in a desiccator. (Yield 20 g.) The white material analyzes for 11.3% Phosphorous (theory 10.85%).

EXAMPLE II

A solution of t-pentylamine (10 g.) in 200 ml isopropanol, is combined dropwise with an alcohol solution of difluorophosphoric acid to acidity. The precipitate is collected, washed with isopropanol and treaturated under anhydrous ethyl ether. After recrystallization 8.1 g. of material analyzing for 16.7% P are obtained (theory 16.37%).

EXAMPLE III 10 g of diaminoheptane dissolved in 500 ml of isopropanol is added of alcoholic difluorophosphoric acid to pH 4. The fine, precipitate is collected, washed and dried. 8.5 g. are thus obtained. A phosphorous analysis shows the material contains 13.03% (theory 13.33%) of this element. Additional material is obtained by evaporation of the solvent.

EXAMPLE IV

To 10 g of diaminoheptane dissolved in 200 ml of methanol there are added with stirring 15.3 g. of monofluorophosphoric acid in 50 ml of methanol. The resulting solution is evaporated to half its volume, and the precipitate that forms on cooling is collected and washed with cold methanol-isopropanol (1:1). 5.3 g. of solid material are obtained. The product is recrystallized from isopropanol-methanol and analyzes for 18.97% P (theory for the dimonofluorophosphate 18.75%P).

EXAMPLE V 10 g of monofluorophosphoric acid dissolved in 30 ml of isopropanol are added dropwise to a solution of 10.2 g. of hexylamine in 100 ml of isopropanol. The solution is concentrated at 40° under reduced pressure. The residue is covered with acetone-ether and allowed to solidify. The crystalline material analyzes for 15.34%P (theory 15.39%).

EXAMPLE VI

To 72.16 g of dimethylamine (25% aqueous solution) in 200 ml. of isopropanol there is added dropwise, at 5° C, a solution of 40.8 g. of difluorophosphoric acid in 200 ml. of isopropanol. The solution is concentrated to dryness under reduced pressure. The residue is then dissolved in ethanol and the solvent distilled to remove any traces of moisture. Upon evaporation under reduced pressure 52 g. of pale yellow viscous liquid are obtained and placed 48 hours in a dessicator in presence of sulfuric acid. The sample analyzes for 21.28%P (theory 21.06%).

EXAMPLE VII 5.9 g. of propylamine in 200 ml of anhydrous ether are treated at 5° with a cold solution of difluorophosphoric acid (10.2 g) in ether. An oil separates. The solvent is decanted and fresh anhydrous ether is added, stirred and decanted. This procedure is repeated twice. The residue is freed of the remaining solvent under reduced pressure, then placed in a dessicator over sulfuric acid and under vacuum. Yield 12.3 g. of viscous oil. %P 19.30 (theory 19.22%).

The efficacy of the materials of the present invention in the prevention of dental caries is demonstrated by measuring the acid solubility reduction of formulations containing the amine mono- and difluorophosphates described in this invention.

Following the procedures described below the measurements for the acid solubility reduction activity of several formulations of the present invention were determined.

50 mg of powdered hydroxyapatite (HAP) was exposed for 10 minutes to 10 ml of an aqueous solution in which was dissolved the material to be tested. The sample was centrifuged and the supernatant discarded. The HAP was washed twice with water and then exposed to acetic acid (pH=3) for 10 minutes. The slurry was filtered and the filter retained the undissolved HAP. As a control, 50 mg HAP that had been pretreated with water was also exposed to acetic acid (pH=3) for 10 minutes and filtered. All filtrates were assayed for solubilized phosphate by the Fiske-Subarrow procedure as follows: to a 0.2 ml aliquot of the filtrate there was added 4.8 ml of 0.5N $H_2SO_4$, followed by 0.7 ml of molybdate reagent (3g. ammonium molybdate, 90 ml water, 16 ml sulfuric acid) and 0.3 ml reducing agent (1.0% 2,4-diaminophenol dihydrochloride in 10% aqueous $NaHSO_3$). After 5 minutes the resulting color was measured spectrophotometrically to determine the amount of phosphate solubilized by the acid. The percent reduction in acid solubility was determined with reference to the control.

A similar procedure as detailed below employing whole extracted human teeth in lieu of HAP was used to demonstrate the effectiveness of the compounds of the present invention.

A clean extracted human tooth is exposed to acetic acid (pH3) for 10 min., then the liquid is transferred into another test tube. This solution serves as control. The tooth is then washed three times with distilled water and then immersed in the test solution for 10 minutes. The supernatant is discarded, the tooth washed three times with distilled water and immersed in 10 ml. of acetic acid (pH3) for 10 minutes. The inorganic phosphate content of the test solution is then compared to the control. The determination of the inorganic phosphate is executed by the Fiske-Subarrow procedure as described above.

The following table sets out the results obtained in reducing the acid solubility of HAP and human teeth employing the alkylamine fluorophosphates of the present invention.

| COMPOUND | % Conc. | pH | % Reduction HAP | % Reduction Teeth |
|---|---|---|---|---|
| laurylamine monofluorophosphate | 1% | 5.52 | 22.7 | |
| laurylamine difluorophosphate | 2.5% | 4.36 | 59.0 | 42.0 |
| t-pentylamine monofluorophosphate | 1% | 4.48 | 51.0 | 30.5 |
| | 4% | 4.43 | 55.9 | 43.5 |
| | 10% | 4.40 | 56.9 | 47.7 |
| t-pentylamine difluorophosphate | 1% | 5.00 | 39.2 | 38.8 |
| | 4% | 5.00 | 46.1 | 45.3 |
| | 10% | 5.00 | 47.7 | 52.1 |
| hexylamine monofluorophosphate | 1% | 5.03 | 58.9 | 47.7 |
| | 4% | 5.00 | 59.7 | 53.2 |
| | 10% | 4.99 | 61.9 | 53.6 |
| hexylamine difluorophosphate | 1% | 4.59 | 62.5 | 82.2 |
| | 4% | 4.60 | 69.5 | 90.7 |
| | 10% | 4.61 | 73.1 | 90.4 |
| octadecylamine monofluorophosphate | 0.1% | 6.18 | 16.7 | 27.6 |
| 1,7-diaminoheptane difluorophosphate | 1% | 6.08 | 40.2 | 28.3 |
| | 4% | 5.71 | 47.1 | 34.4 |
| | 10% | 5.51 | 54.9 | 45.3 |
| 1,7-diaminoheptane-di-monofluorophosphate | 1% | 4.59 | 64.1 | 62.9 |
| | 4% | 4.60 | 67.2 | 66.2 |
| | 10% | 4.58 | 68.4 | 70.5 |
| 1,10-diaminodecane monofluorophosphate | 1% | 5.06 | 41.6 | 29.3 |
| | 4% | 4.87 | 48.1 | 36.8 |
| | 10% | 4.75 | 57.1 | 47.0 |
| dimethylamine difluorophosphate | 1% | 4.14 | 61.9 | 67.5 |
| | 5% | 4.52 | 72.4 | 73.8 |
| | 10% | 4.70 | 91.3 | 88.4 |
| propylamine difluorophosphate | 1% | 5.00 | 60.0 | 65.4 |
| | 5% | 5.00 | 84.0 | 88.0 |
| | 10% | 5.02 | 90.9 | 92.1 |
| triethanolamine difluorophosphate | 1% | 4.56 | 58.9 | |
| | 5% | 4.52 | 60.9 | |
| | 10% | 4.56 | 64.6 | |

The compositions of the present invention can be applied to the teeth in solid or liquid form in conjunction with any carrier suitable for oral use. Thus the alkylamine fluorophosphates may be combined in a mouthwash, a tooth paste, a tooth powder, etc. The preferred method of application is in the form of a mouthwash which would be used after brushing the teeth. The mouthwash composition usually includes water and a dispersing agent such as alcohol as well as other ingredients such as penetrants, astringents, flavors, other therapeutic or preventative compounds. There is a virtually unlimited choice of mouthwash formulations available to those skilled in the art and the following formulation is offered as being representative only.

The following formulations are typical examples of mouthwash formulations including the novel alkylamine fluorophosphates of the present invention.

| Ingredient | Formulation 1 (parts by weight) | Formulation 2 (parts by weight) |
|---|---|---|
| DMA-DFP* | 4.0 | 4.0 |
| Propylene Glycol | 15.0 | — |
| Ethanol | 5.0 | 10.0 |
| Sorbo | — | 20.0 |
| Pluronic F-88 | 0.4 | — |
| Tween 60 | — | 0.3 |
| Citric Acid | — | 0.1 |
| Water | 75.6 | 65.6 |
| | 100.0 | 100.0 |

*dimethylamine difluorophosphate

Numerous modifications and variations of the present invention will be obvious to those skilled in the art in light of the foregoing specification and the invention may be practiced in a manner other than as specifically set forth and still fall within the scope of the appended claims.

What is claimed is:

1. Alkylamine fluorophosphates of the formula:

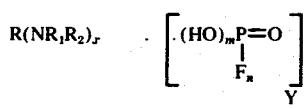

wherein R is a linear or branched alkyl group containing 1–20 carbon atoms, $R_1$ is hydrogen or lower alkyl containing 1–6 carbon atoms, $R_2$ is hydrogen or lower alkyl, $x$ is 1 or 2, $m$ and $n$ are whole integers whose sum is 3 and Y is 1 when $x=1$ and 1 or 2 when $x=2$; when R, $R_1$ and $R_2$ are lower alkyl they can be substituted with an hydroxy group.

2. Dimethylamine difluorophosphate.
3. Propylamine difluorophosphate.
4. Hexylamine mono or difluorophosphate.
5. 1,7-diaminoheptane mono or difluorophosphates
6. A dental prophylaxis comprising a vehicle and an alkylamine fluorophosphate of the formula:

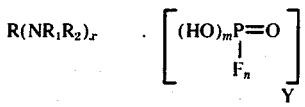

wherein R is a linear or branched alkyl group containing 1–20 carbon atoms, $R_1$ is a lower alkyl of 1–6 carbon atoms or hydrogen $R_2$ is hydrogen or lower alkyl, $x$ is 1 or 2, Y is 1 when $x$ is 1, Y is 1 or 2 when $x=2$, and $m$ and $n$ are whole positive integers whose sum is 3. When R, $R_1$ and $R_2$ represent a lower alkyl they can be substituted with an hydroxy group.

7. Dental prophylaxis according to claim 6 wherein the alkylamine fluorophosphate is a difluorophosphate of dimethylamine.
8. Dental prophylaxis according to claim 6 wherein the alkylamine fluorophosphate is a difluorophosphate of propylamine.
9. Dental prophylaxis according to claim 6 wherein the alkylamine fluorophosphate is a mono- or difluorophosphate of hexylamine.
10. Dental prophylaxis according to claim 6 wherein the alkylamine fluorophosphate is a mono- or difluorophosphate of 1,7-diaminoheptane.
11. Dental prophylaxis according to claim 6 wherein the alkylamine fluorophosphate is a mono- or dilfuorophosphate of t-pentylamine.
12. Dental prophylaxis according to claim 6 wherein the fluorophosphate is triethanolamine diflorophosphate.
13. A method for preventing dental caries which comprises coating the teeth with a prophylactic amount of an alkylamine fluorophosphate of the formula:

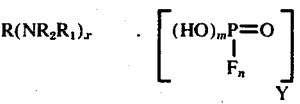

wherein R is a linear or branched alkyl group containing 1–20 carbon atoms, $R_1$ is hydrogen or lower alkyl containing 1–6 carbon atoms, $R_2$ is hydrogen or lower alkyl, $x$ is 1 or 2, Y is 1 when $x$ is 1, Y is 1 or 2 when $x=2$; $m$ and $n$ are whole positive integers whose sum is 3. When R, $R_1$, $R_2$ are alkyl they can be substituted with an hydroxy radical.

14. T-Pentylamine mono or difluorophosphates.
15. Laurylamine mono or difluorophosphates.
16. Triethanolamine difluorophosphates.

* * * * *